US007008401B2

(12) United States Patent
Thompson et al.

(10) Patent No.: US 7,008,401 B2
(45) Date of Patent: Mar. 7, 2006

(54) ASSEMBLIES FOR CREATING COMPOUND CURVES IN DISTAL CATHETER REGIONS

(75) Inventors: Russell B. Thompson, Los Altos, CA (US); Sidney D. Fleischman, Menlo Park, CA (US); James G. Whayne, Saratoga, CA (US); David K. Swanson, Mountain View, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 140 days.

(21) Appl. No.: 10/057,478

(22) Filed: Jan. 22, 2002

(65) Prior Publication Data

US 2002/0068868 A1 Jun. 6, 2002

Related U.S. Application Data

(60) Continuation of application No. 09/054,257, filed on Apr. 2, 1998, now Pat. No. 6,602,278, which is a continuation of application No. 08/645,456, filed on May 13, 1996, now Pat. No. 5,820,591, which is a continuation-in-part of application No. 08/625,724, filed on Mar. 29, 1996, now abandoned, which is a continuation of application No. 08/099,603, filed on Jul. 30, 1993, now Pat. No. 5,395,327, which is a continuation of application No. 07/991,474, filed on Dec. 16, 1992, now Pat. No. 5,254,088, which is a continuation of application No. 07/736,384, filed on Jul. 26, 1991, now abandoned, which is a division of application No. 07/473,667, filed on Feb. 2, 1990, now abandoned.

(51) Int. Cl.
*A61M 37/00* (2006.01)

(52) U.S. Cl. .................................. 604/95.04; 604/528

(58) Field of Classification Search ............. 604/95.04, 604/96.01, 105, 523–524, 528, 530–539, 604/99, 95; 606/41, 46–47, 49; 607/99; 600/374

See application file for complete search history.

(56) References Cited

U.S. PATENT DOCUMENTS

| 5,055,101 A | 10/1991 | McCoy |
| 5,090,956 A | 2/1992 | McCoy |
| 5,114,402 A | 5/1992 | McCoy |
| 5,190,050 A | 3/1993 | Nitzsche |
| 5,254,088 A | 10/1993 | Lundquist et al. |
| 5,306,245 A * | 4/1994 | Heaven ..................... 604/523 |
| 5,322,064 A * | 6/1994 | Lundquist ................... 600/381 |

(Continued)

FOREIGN PATENT DOCUMENTS

EP 0605796 A2 7/1994

(Continued)

OTHER PUBLICATIONS

Preliminary Report on a New Method of Intestinal Intubation With The Aid of a Flexible Stylet With Controllable Tip, Smith et al., Surgery, vol. 27, No. 6, Jun. 1950, pp. 817-821.

*Primary Examiner*—Nicholas D. Lucchesi
*Assistant Examiner*—Laura A. Bouchelle
(74) *Attorney, Agent, or Firm*—Henricks, Slavin & Holmes LLP (57) ABSTRACT

Compound steering assemblies, usable in both diagnostic and therapeutic applications, enable a physician to swiftly and accurately steer the distal section of the catheter in multiple planes or complex curves to position and maintain ablation and/or mapping electrodes in intimate contact with an interior body surface.

36 Claims, 11 Drawing Sheets

U.S. PATENT DOCUMENTS

| | | |
|---|---|---|
| 5,328,467 A | 7/1994 | Edwards et al. |
| 5,334,145 A | 8/1994 | Lundquist et al. |
| 5,336,182 A | 8/1994 | Lundquist et al. |
| 5,358,479 A | 10/1994 | Wilson |
| 5,372,587 A | 12/1994 | Hammerslag et al. |
| 5,383,852 A | 1/1995 | Stevens-Wright |
| 5,383,923 A | 1/1995 | Webster, Jr. |
| 5,395,327 A | 3/1995 | Lundquist et al. |
| 5,482,037 A | 1/1996 | Borghi |
| 5,571,085 A | 11/1996 | Accisano, III |
| 5,626,136 A | 5/1997 | Webster, Jr. |
| 5,642,736 A | 7/1997 | Avitall |
| 5,673,695 A | 10/1997 | McGee et al. |
| 5,676,662 A | 10/1997 | Fleischhacker et al. |
| 5,738,683 A | 4/1998 | Osypka |
| 5,779,669 A | 7/1998 | Haissaguerre et al. |
| 5,782,828 A | 7/1998 | Chen et al. |
| 5,820,591 A * | 10/1998 | Thompson et al. ...... 604/95.01 |
| 5,820,592 A | 10/1998 | Hammerslag |
| 5,891,088 A | 4/1999 | Thompson et al. |
| 6,413,234 B1 * | 7/2002 | Thompson et al. ...... 604/95.04 |
| 6,602,278 B1 | 8/2003 | Thompson et al. |
| 6,613,046 B1 * | 9/2003 | Jenkins et al. ................ 606/41 |
| 6,645,200 B1 * | 11/2003 | Koblish et al. ............... 606/41 |

FOREIGN PATENT DOCUMENTS

| | | |
|---|---|---|
| EP | 0609182 A1 | 8/1994 |
| WO | WO 91/11213 A1 | 8/1991 |

* cited by examiner

ASSEMBLIES FOR CREATING COMPOUND CURVES IN DISTAL CATHETER REGIONS

CROSS REFERENCE TO RELATED APPLICATIONS

This application is a continuation of U.S. application Ser. No. 09/054,257, filed Apr. 2, 1998 now U.S. Pat. No. 6,602,278, which is a continuation of U.S. application Ser. No. 08/645,456, filed May 13, 1996, now U.S. Pat. No. 5,820,591, which is a continuation-in-part of application Ser. No. 08/625,724, filed Mar. 29, 1996, now abandoned, which is a continuation of application Ser. No. 08/099,603, filed Jul. 30, 1993, now U.S. Pat. No. 5,395,327, which is a continuation of application Ser. No. 07/991,474, filed Dec. 16, 1992, now U.S. Pat. No. 5,254,088, which is a continuation of application Ser. No. 07/736,384, filed Jul. 26, 1991, now abandoned, which is a divisional of application Ser. No. 07/473,667, filed Feb. 2, 1990, now abandoned.

FIELD OF THE INVENTION

This invention relates to catheters that can by steered by external controls. More particularly the invention relates to such catheters that can assume complex three dimensional curves. In addition, the invention relates to the use of such complex curves to ablate arrhythmia substrates in body tissue.

BACKGROUND OF THE INVENTION

Cardiac mapping is used to locate aberrant electrical pathways and currents emanating within the heart. Such aberrant pathways cause irregular contractions of the heart muscle resulting in life-threatening patterns or disrhythmias.

Ablation of cardiac tissue to create long curvilinear lesions within the heart is also desired for treatment of various disorders such as atrial fibrillation. Various steering mechanisms for catheters carrying such electrodes have heretofore been developed and used.

To access various endocardial sites, physicians have used a number of different catheters and techniques, each of which provides a different characteristic. The use of catheters having limited steering characteristics increases the risk inherent in any catheterization procedure and limits the accessibility of many potential ablation sites.

Site access using standard distal tip steerable catheters is less of a problem because those catheters position a single electrode into contact with the endocardium and a specific electrode orientation is not required. Problems of endocardial site access are accentuated when trying to simultaneously position multiple electrodes into intimate tissue contact. In this scenario, standard steerable catheter configurations orient multiple electrodes in planes emanating about the axis of the introduction vessel.

A need has thus existed for catheters which, in the nonlinear environment found within the heart as well as other body cavities, are capable of being steered to place ablation elements at a number of locations while creating intimate tissue contact throughout the length of all active ablation elements.

Particularly, a need has existed for a catheter which could effectively and accurately form curves in more than one plane for better access or tissue contact. Previous attempts to provide such devices are represented by U.S. Pat. No. 5,383,852 wherein there was suggested the use of steering wire extending from a central lumen of a catheter radially outward to the periphery of a distal end component. Another suggestion in represented by U.S. Pat. No. 5,358,479 wherein a single pull cable is attached to the distal end of a shim which has two flat sections that are twisted relative to each other. This arrangement, however limits the device to bending, first, of the more distal portion of the shim followed by subsequent bending of the more proximal section, thus limiting the procedures using the device.

SUMMARY OF THE INVENTION

The present inventions provides a catheter, usable in both diagnostic and therapeutic applications, that enables a physician to swiftly and accurately steer the distal section of the catheter containing the ablation and/or mapping element(s) in multiple planes or complex curves within the body of a patient. The catheters that embody the invention allows physicians to better steer a catheter to access various endocardial sites. In its broadest aspect, the invention provides catheters which enable a physician to position ablation and/or mapping electrodes inserted within a living body by manipulation of external controls into intimate contact with an interior body surface that curves in more than one plane.

One aspect of the invention provides a catheter having more than one steering mechanism for bending the distal section by external manipulation into more than one curvilinear direction. Movement of the individual controls results in bending of the distal section at more than one location and in more than one direction. Thus the ease of accessing and measuring electrical activity in all portions of the heart is increased.

In accordance with another embodiment, the catheter steering assembly may include a proximal section containing a preformed portion in conjunction with a distal steering mechanism which enables steering in a different plane that is non-parallel to the bending plane of the preformed proximal section, and/or improving tissue contact by moving the focal point of the steering mechanism to increase the angle of steering capable of applying force against the endocardial surface. This configuration may be accomplished by preforming the proximal section of the catheter into the desired curve or manipulating a preformed wire or other support structure which, when freed from the constraints of a sheath such as the catheter main body, causes the proximal section to assume the preformed shape.

In accordance with a further embodiment of the invention, a loop catheter has a preformed proximal end and a moveable wire attached to the distal end of the spline housing the ablation element(s). The preformed proximal end enables the loop to access varying planes relative to the catheter axis.

Further, objects and advantages of the invention will become apparent from the following detailed description and accompanying drawings.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF PREFERRED EMBODIMENTS

This Specification discloses electrode-carrying structures that can be bent in compound and complex manners for greater maneuverability within the body and enhanced contact with tissue. The illustrated and preferred embodiments discuss these structures, systems, and techniques in the context of catheter-based cardiac ablation. That is because these structures, systems, and techniques are well suited for use in the field of cardiac ablation.

Still, it should be appreciated that the invention is applicable for use in other tissue ablation applications. For example, the various aspects of the invention have application in procedures for ablating tissue in the prostrate, brain, gall bladder, uterus, and other regions of the body, using systems that are not necessarily catheter-based.

Figure 1:
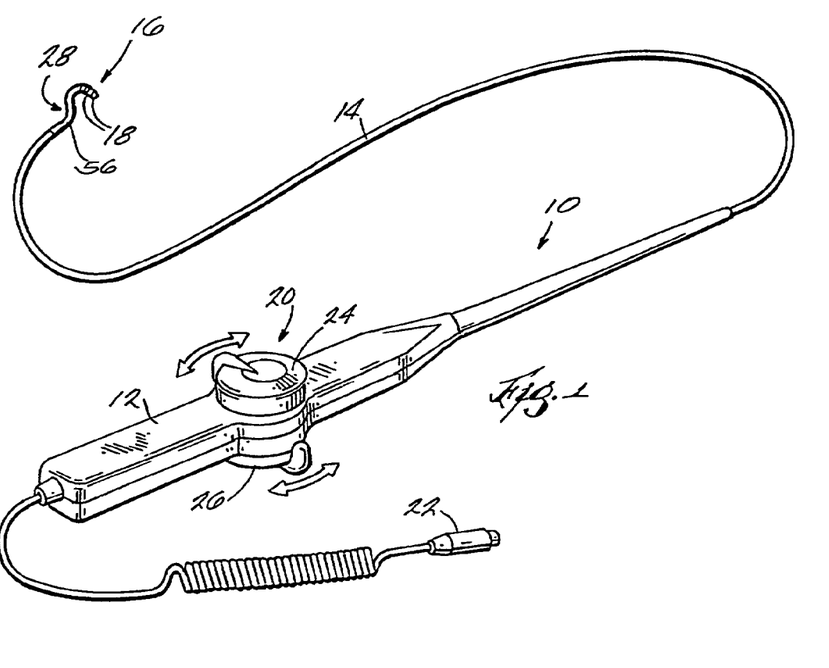
FIG. 1 is a perspective view of a catheter having a distal region with a compound steering assembly that embodies features of the invention.

FIG. 1 shows a catheter 10, which embodies features of the invention. The catheter 10 includes a handle 12 and a flexible catheter body 14. The distal region 16 of the catheter body 14 carries at least one electrode 18. In the illustrated and preferred embodiment, the distal region 16 carries an array of multiple electrodes 18.

The electrodes 18 can serve to monitor electrical events in heart tissue, or transmit electrical energy to ablate heart tissue, or both. Signal wires (not shown) are electrically coupled to the electrodes 18 in conventional fashion. The signal wires extend through the catheter body 14 into the handle 12. The signal wires electrically connect to an exterior plug 22, which can be connected to signal processing equipment or a source of electrical ablation energy, or both.

The catheter 10 shown in FIG. 1 includes a steering mechanism 20. The mechanism 20 includes two control knobs 24 and 26 on the handle 12, which can be individually manipulated by the physician.

As will be described in greater detail later, the steering mechanism 20 is coupled to a compound steering assembly 28, which is carried within the distal region 16 of the catheter body 14. Operation of the control knobs 24 and 26 bend the steering assembly 28 to flex the distal region 16 (as FIG. 1 generally shows) in ways that aid in orienting the ablation element 18 in intimate contact with tissue.

Figure 3:
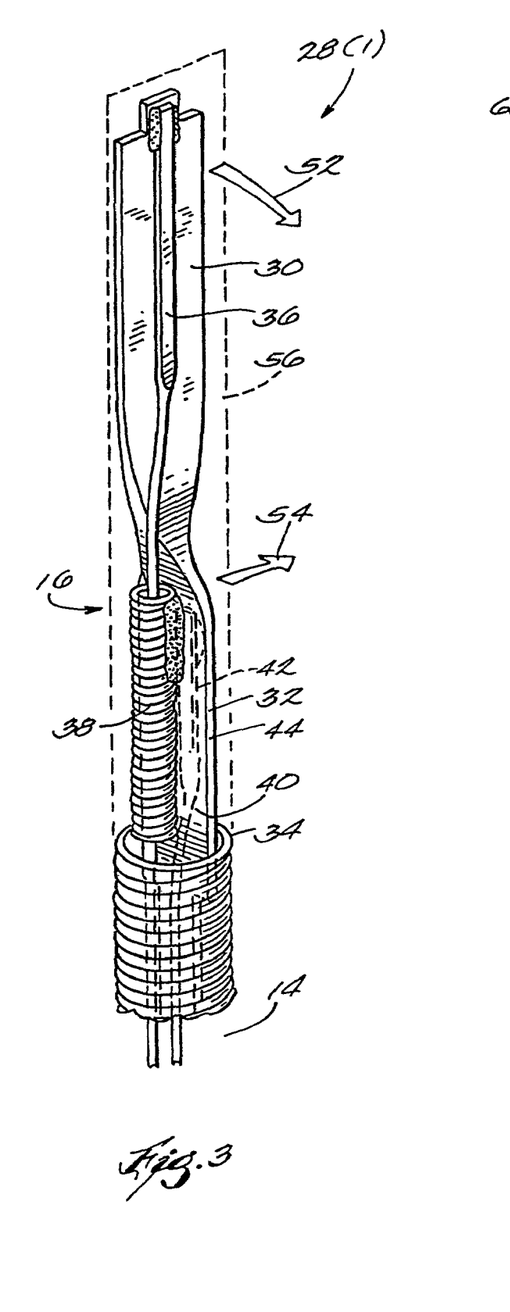
FIG. 3 is a perspective view of one embodiment of a compound steering assembly that embodies features of the invention.

FIG. 3 shows one embodiment of a compound steering assembly, designated by reference numeral 28(1), that embodies features of the invention. The compound steering assembly 28(1) includes a spring element formed as a single piece in two bendable sections 30 and 32. The bendable section 30 is distal to the bendable section 32.

In the illustrated embodiment, the bendable sections 30 and 32 are arranged essentially orthogonally relative to each other, being offset by about 90°. Different offset angles between 0° and 180° may be used.

The proximal end of the proximal bendable section 32 is secured within a guide tube 34. In the illustrated embodiment, the guide tube 34 takes the form of a coiled stainless steel spring. The guide tube 34 extends from the steering assembly 28(1) rearward within the catheter body 14 to the handle 12. The guide tube 34 serves to stiffen the catheter body 14 and to help impart twisting motion from the handle to the steering assembly 28(1).

As FIG. 3 shows, a distal steering wire 36 is attached by soldering or adhesive to one surface of the distal bendable section 30. The steering wire 36 extends from the bendable section 30 through a guide tube 38 secured by soldering or adhesive to a surface 40 of the proximal bendable section 32. From there, the steering wire 36 extends through the guide tube 34 into the handle 12. The steering wire 36 is coupled to the control knob 24 within the handle 12, as will be described in greater detail later.

A proximal steering wire 42 is attached by soldering or adhesive to the surface 44 of the proximal bendable section 32 opposite to the surface 40. From there, the steering wire 42 extends through the guide tube 34 into the handle 12. The steering wire 42 is coupled to the control knob 26 within the handle 12, as will be described in greater detail.

Flexible heat shrink tubing 56 (shown in FIG. 1 and in phantom lines in FIG. 3) encloses the compound steering assembly 28(1).

Figure 2:
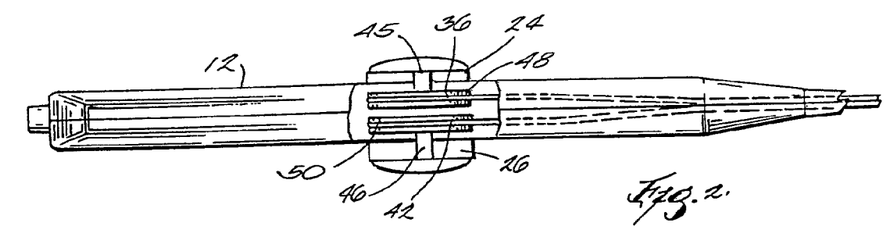
FIG. 2 is a fragmentary side view of the handle portion of the catheter shown in FIG. 1.

As FIG. 2 shows, the control knobs 24 and 26 are individually coupled by shafts, respectively 45 and 46, to rotatable cam wheels, respectively 48 and 50, within the handle 12. Rotation of the respective knob 24 and 26 serves to rotate its respective cam wheel 48 and 50. The steering wire 36 is attached to the cam wheel 48, and the steering wire 42 is attached to the cam wheel 50.

Further details of the structure of the cam wheels 48 and 50 and their attachment to the steering wires 36 and 42 are not essential to the invention and can be found in U.S. Pat. No. 5,254,088, which is incorporated herein by reference.

Rotation of the cam wheel 48 (by manipulation of the knob 24) pulls upon the distal steering wire 36. This, in turn, pulls upon the distal bendable section 30, flexing the bendable section 30 in the direction of the wire 36 (shown by arrow 52 in FIG. 3). The guide tube 38 facilitates movement of the steering wire 36 and the transmission of the pulling force from the cam wheel 48 to the bendable section 30. In the absence of the pulling force upon the wire 36, the bendable section 30 resiliently returns to its normal unbent condition (shown in FIG. 3).

Likewise, rotation of the cam wheel 50 (by manipulation of the knob 26) pulls upon the steering wire 42. This, in turn, pulls upon the proximal bendable section 32, flexing the bendable section 32 in the direction of the wire 42 (as arrow 54 shows in FIG. 3). In the absence of the pulling force upon the wire 42, the bendable section 32 resiliently returns to its normal unbent condition (as FIG. 3 shows).

In the illustrated and preferred embodiment, the guide tube 38 comprises a stainless steel coil. As a steel coil, the guide tube 38 provides bending resistance and bias for the assembly 28(1) to return to the unbent orientation after deflection.

The compound steering assembly 28(1) makes possible the formation of complex curves in the distal region 16. Pulling on the distal wire 36 bends the distal region 16 in the direction 52. Pulling on the proximal steering wire 42 further bends the distal region 16 in a different direction 55.

FIG. 3 shows a single steering wire 36 and 42 attached to each bendable section 30 and 32 to provide unidirectional bending of each section 30 and 32. Of course, either or both bendable sections 30 and 32 may include an opposing pair of steering wires (not shown) to provide bidirectional bending action. If bidirectional bending of the distal section 30 is desired, a guide tube 38 is preferably provided for each steering wire attached to the section 30. In this arrangement, the guide tubes should preferably comprise a material at least as flexible as the proximal section 32 itself, so as to not impede the desired bending action.

Figure 4:
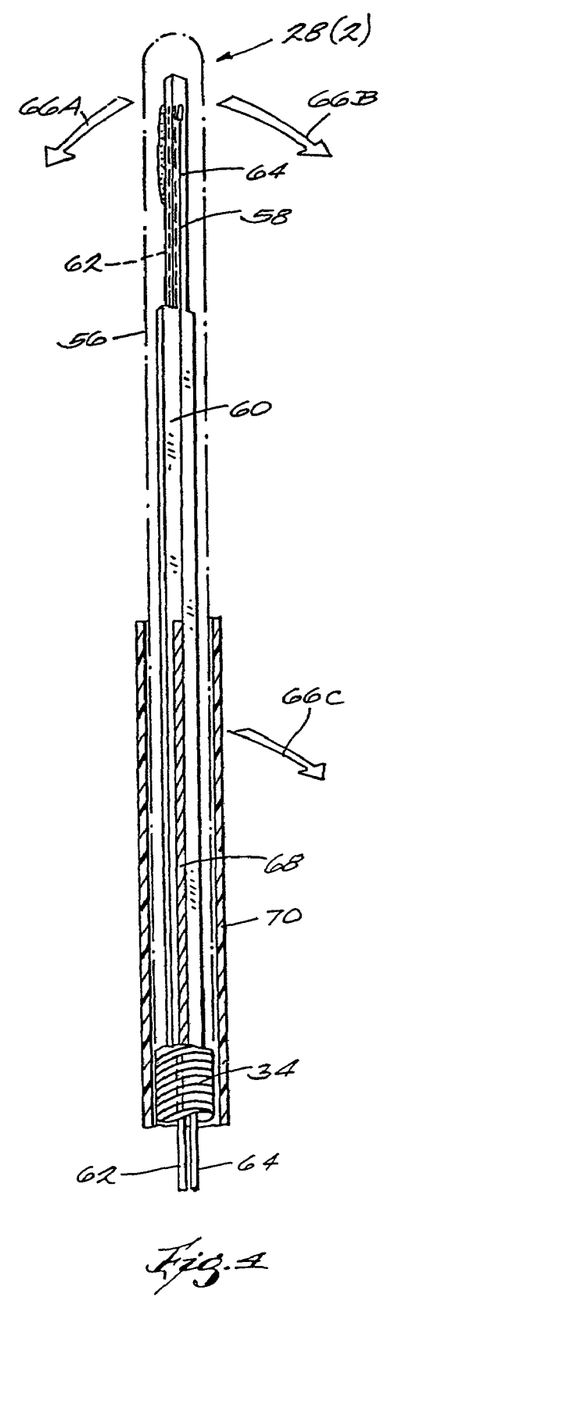
FIG. 4 is a side section view of another embodiment of a compound steering assembly that embodies features of the invention.

FIG. 4 shows an alternative embodiment of a compound steering assembly, designated 28(2). The compound steering assembly 28(2) includes a spring element formed as a single piece in two bendable sections 58 and 60. The bendable section 58 is distal to the bendable section 60.

Like the embodiment shown in FIG. 3, the proximal end of the bendable section 60 is secured within a guide tube 34. Unlike the embodiment shown in FIG. 3, the bendable sections 58 and 60 are not offset from each other, but extend in the same plane.

A pair of steering wires 62 and 64 are attached to opposite surfaces of the distal bendable section 58. The steering wires 62 and 64 extend rearward through the guide tube 34 within the catheter body 14 for attachment to opposite sides of a rotatable cam wheel (not shown) within the handle 12. U.S. Pat. No. 5,254,088 shows the details of this construction, which is incorporated herein by reference. Rotation of the cam wheel in one direction pulls on the steering wire 62 to bend the distal section 58 in one direction (shown by arrow 66A in FIG. 4). Rotation of the cam wheel in the opposite direction pulls on the steering wire 64 to bend the distal section 58 in the opposite direction (shown by arrow 66B in FIG. 6). Bi-directional steering of the distal section 58 is thereby achieved.

The compound steering assembly 28(2) shown in FIG. 4 further includes a preformed wire 68 secured by soldering or adhesive to the proximal bendable section 60. The preformed wire 68 is biased to normally curve. The preformed wire 68 may be made from stainless steel 17/7, nickel titanium, or other memory elastic material. It may be configured as a wire or as a tube with circular, elliptical, or other cross-sectional geometry.

The wire 68 normally imparts its curve to the attached bendable section 60, thereby normally bending the section 60 in the direction of the curve. The direction of the normal bend can vary, according to the functional characteristics desired. The wire 68 can impart to the section a bend in the same plane as the distal bendable section 58 (as shown by arrow 66C in FIG. 4), or in a different plane.

In this arrangement, the steering assembly 28(2) further includes a main body sheath 70. The sheath 70 slides along the exterior of the catheter body 14 between a forward position overlying the junction between the wire 68 and proximal bendable section 60 and an aft position away from the proximal bendable section 68. In its forward position, the sheath 70 retains the proximal bendable section 60 in a straightened configuration against the normal bias of the wire 68, as FIG. 4 shows. The sheath 70 may include spirally or helically wound fibers to provide enhanced tensile strength to the sheath 70. Upon movement of the sheath 70 to its aft position, the proximal bendable section 60 yields to the wire 68 and assumes its normally biased bent position. The slidable sheath 70 is attached to a suitable control mechanism on the handle 12.

Figure 5A:
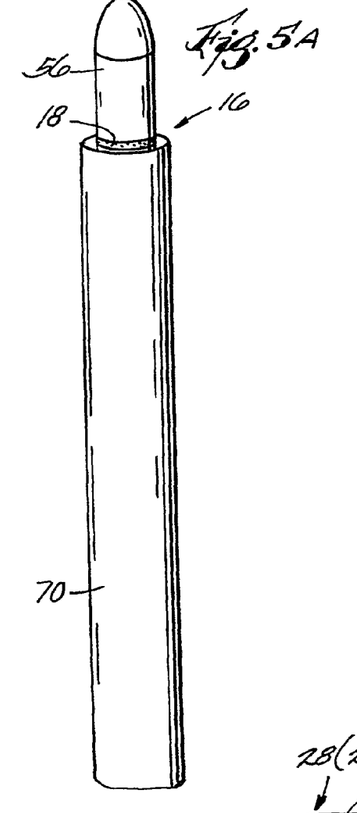
FIGS. 5A to 5C are side views, with portions broken away and in section, of the compound steering assembly shown in FIG. 4 in use.
Figure 5B:
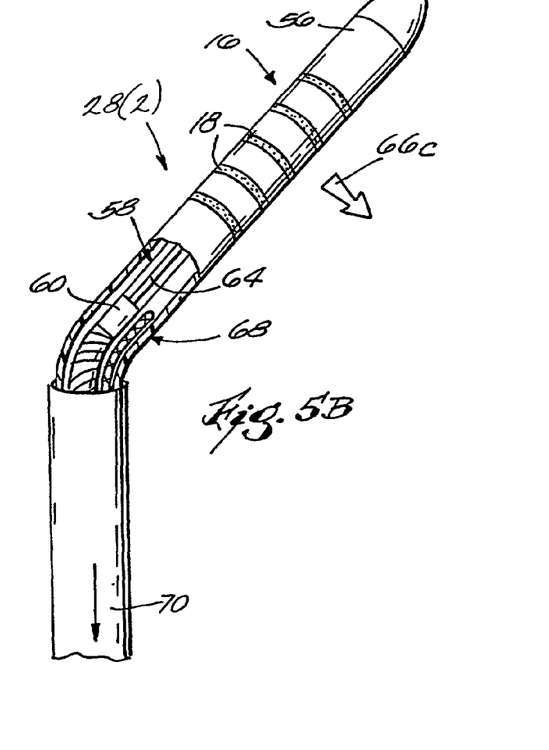
Figure 5C:
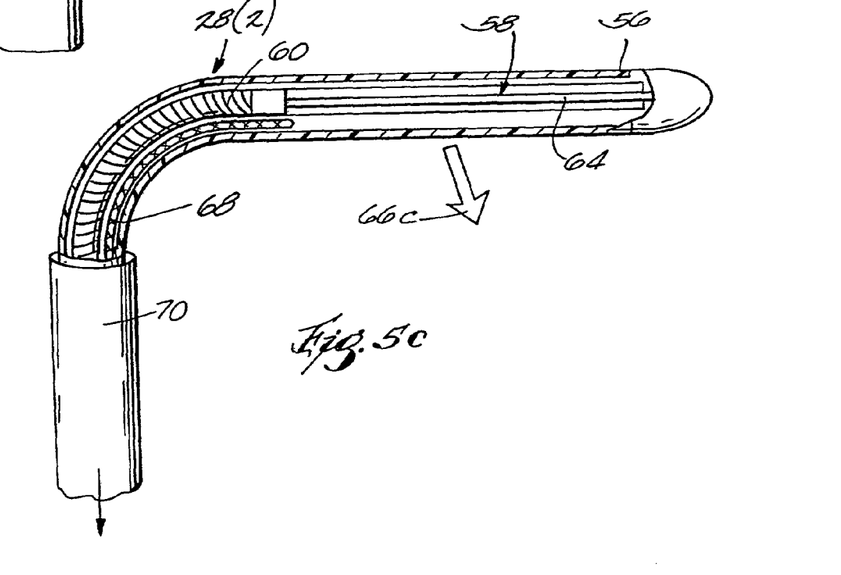

As FIG. 5A shows, during introduction of the proximal catheter region 16 into the body, the sheath 70 is retained in its forward position. This retains the proximal bendable section 60 in a substantially straight orientation (as FIG. 4 also shows). After introduction of the distal catheter region 16 into a desired heart chamber, the sheath 70 is withdrawn (as shown in a stepwise fashion by FIGS. 5B and 5C). The wire 68 urges the proximal bendable section 60 to assume a curvature in the direction indicated by arrow 66C.

The embodiment of FIGS. 4 and 5A/B/C provides compound curves. The amount of curvature of the preshaped wire 68 is selected in accordance with the projected shape of the body chamber into which the catheter is introduced. Further bending of the distal section 58 is accomplished by pulling on the steering wires 62 and 64.

It should be appreciated that, instead of a stationary preshaped wire 68 and movable sheath 70, the steering assembly 28(2) can include a precurved stylet 72 (see FIGS. 6A to 6C) moveable along the proximal bendable section 60 within a stationary sheath 74. A mechanism (not shown) mounted in the handle affects movement of the stylet 72 under the control of the physician. The stationary sheath 74 extends about the catheter body 14 up to distal region 16.

Figures 6A, 6B, 6C:
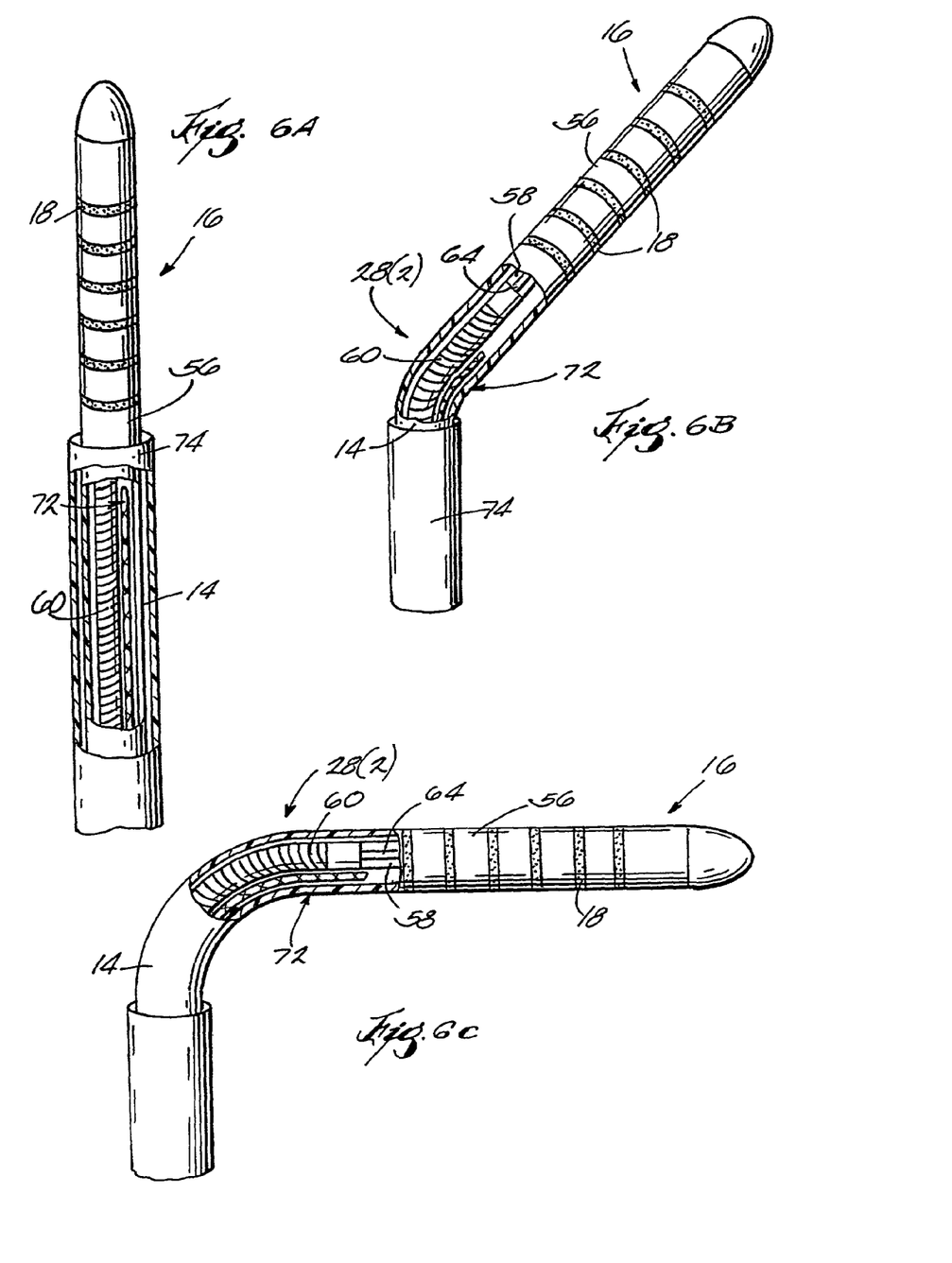
FIGS. 6A to 6C are side views, with portions broken away and in section, of an alternative embodiment of a compound steering assembly that embodies features of the invention being used.

When located within the region of the sheath 74 (as FIG. 6A shows), the stylet 72 is retained by the sheath 74 in a straight condition. When the preshaped stylet 72 is advanced beyond the sheath 74 (as FIGS. 6B and 6C show, the stylet 72 imparts its normal curve to the proximal section 60, causing it to assume a curvature determined by the stylet 72.

Figure 7:
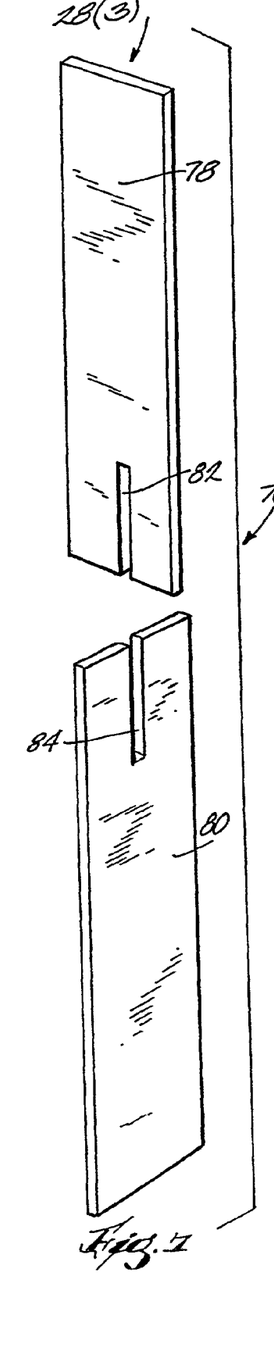
FIG. 7 is an exploded perspective view of a two piece offset spring assembly that forms a part of an alternative embodiment of a compound steering assembly that embodies feature of the invention.
Figure 8:
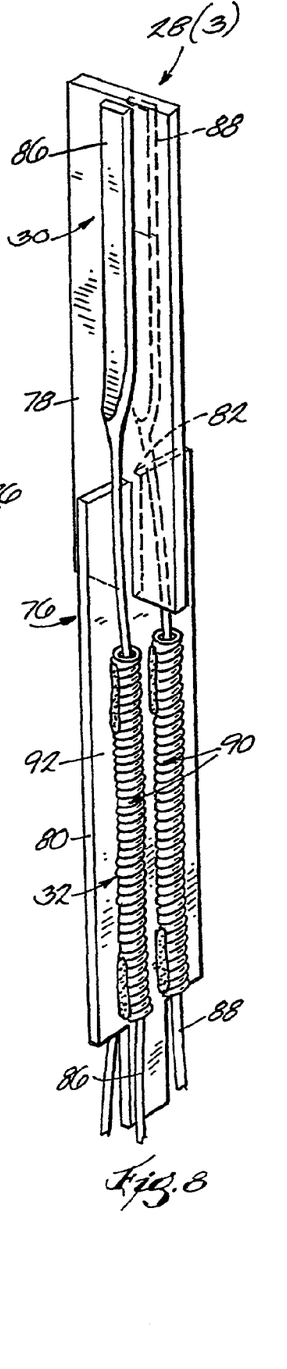
FIGS. 8 and 9 are side perspective views of the compound steering assembly that incorporates the two piece offset spring assembly shown in FIG. 7.
Figure 9:
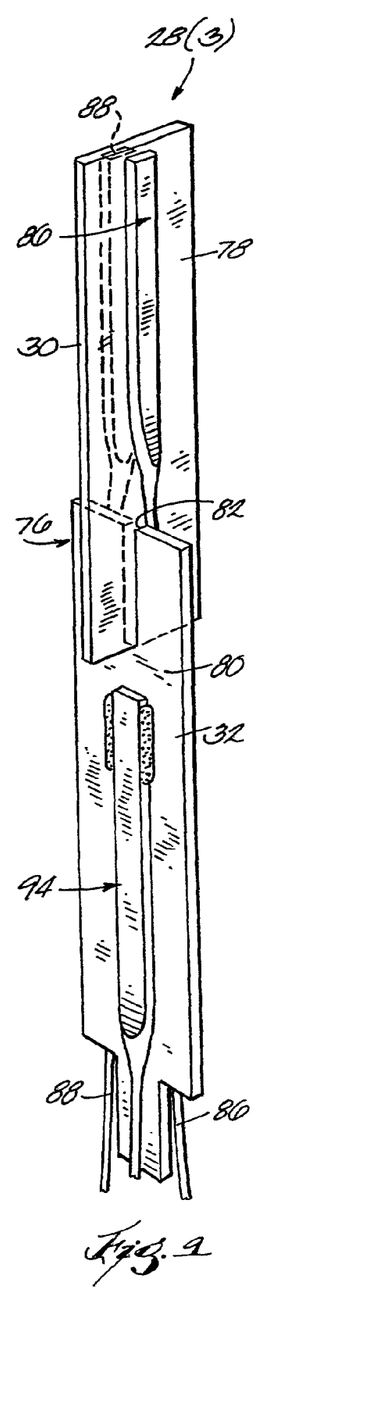

FIGS. 7 to 9 show another alternative embodiment for a compound steering assembly, designated 28(3), embodying features of the invention. The compound steering assembly 28(3) includes a composite spring 76 formed from two individual spring sections 78 and 80 (see FIG. 7). The spring sections 78 and 80 include mating central notches 82 and 84, which nest one within the other to assemble the spring sections 78 and 80 together. Soldering or brazing secures the assembled sections 78 and 80 to complete the composite spring 76.

The resulting composite spring 76, like the spring shown in FIG. 3, comprises a bendable distal section 30 (spring section 78) and a bendable proximal section 32 (spring section 80). The bendable proximal section 32 is secured to a guide coil in the catheter body in the same manner shown in FIG. 3.

As FIG. 8 and 9 further show, the compound steering assembly 28(3) preferably includes two steering wires 86 and 88 attached by soldering or adhesive to opposite surfaces of the distal bendable section 30. The steering wires 86 and 88 each extend from the distal bendable section 30 through a guide tube 90 secured by soldering or adhesive to one surface 92 of the proximal bendable section 32. From there, the steering wires 86 and 88 extend through the main guide tube 34 within the catheter body 14 into the handle 12 for attachment to a control mechanism in the handle, as already described.

As FIGS. 8 and 9 also show, the compound steering assembly 28(3) preferably includes one steering wire 94 attached by soldering or adhesive to the proximal bendable section 32 on the surface opposite to the surface to which the guide tubes 90 are attached. The steering wire 94 likewise passes through guide tube 34 within the catheter body 14 for attachment to a second control mechanism in the handle, as already described.

As also previously described, the guide tubes 90 preferable take the form of metal coils. As coils, the guide tubes 90 provide increased spring bias to aid the return of the proximal bendable section 32 to the straightened position in the absence of pulling force on the steering wire.

The compound steering assembly 28(3) shown in FIGS. 8 and 9 permits flexing the distal bendable section 30 in opposite directions normal to the surface of spring section 78. The compound steering assembly 28(3) also permits independent flexing of the proximal bendable section 32 in a single direction normal to the surface of spring section 80 to which the steering wire 94 is attached.

While the illustrated and preferred embodiment of the proximal bendable section 32 shown in FIGS. 8 and 9 does not permit bidirectional bending, it should be appreciated that two oppositely attached steering wires may be attached to the proximal section 32 to allow bidirectional steering. In this arrangement, the guide tubes 90 should be made of materials no less flexible than the proximal section itself.

Figure 10A:
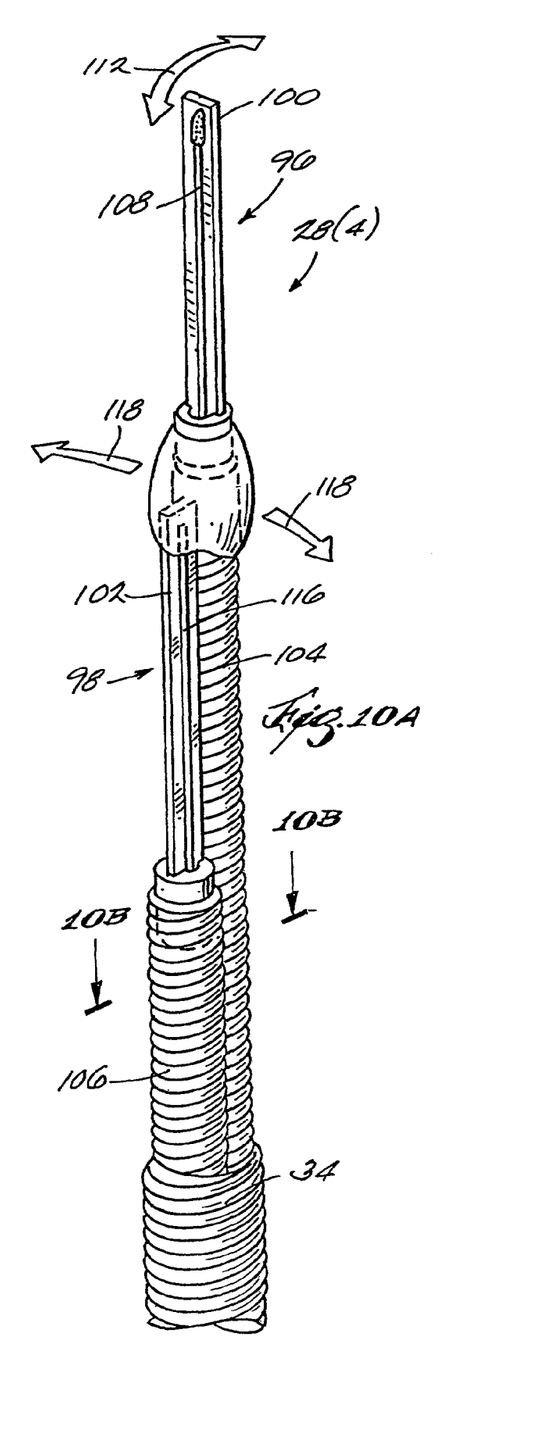
FIG. 10A is a side view of another embodiment of a compound steering assembly that embodies features of the invention.
Figure 10B:
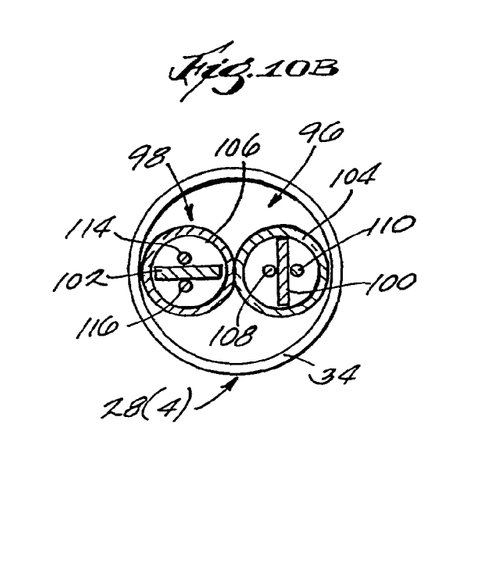
FIG. 10B is a top sectional view of the compound steering assembly shown in FIG. 10A, taken generally along line 10B—10B in FIG. 10A.

FIGS. 10A and 10B show another alternate embodiment of a compounding steering assembly, designated 28(4). The compound steering assembly 28(4) includes two separate steering assemblies 96 and 98 radially offset from each other within the catheter body 14 (see FIG. 10B). Each steering assembly 96 and 98 includes a bendable spring, respectively 100 and 102, carried by relatively small diameter spring coils, respectively 104 and 106. The bendable spring 100 extends distally to the bendable spring 102.

A pair of steering wires 108 and 110 are attached to the opposite sides of the distal steering spring 100 to enable bending in a first plane (shown by arrows 112 in FIG. 10A). A second pair of steering wires 114 and 116 are attached to opposite sides of the proximal steering spring 102 to enable bending in a second plane (shown by arrows 118 in FIG. 10A). As FIG. 10A shows, the small diameter wire coils 104 and 106 may themselves be contained within the larger diameter steering coil 34 within the catheter body 14.

Instead of steering wires 108/110 and 114/116, either or both springs 100 and 102 could be attached to preshaped wires (not shown) to assume a desired curvature, to thereby bend the respective spring in the manner shown in FIG. 4. Alternatively, the compound steering assembly 28(4) may includes a third, preshaped wire section (not shown), like that shown in FIG. 4 located, either proximally or distally to the bendable springs 100 and 102. In these arrangements, an external slidable sleeve (not shown) is used to selectively straighten the preshaped wire when desired. In this way, complex bends can be formed in the distal region in at least 3 different planes, or, alternatively, two bending locations can be provided in a single plane with another bending location being provided in an orthogonally separate plane.

Figure 11:
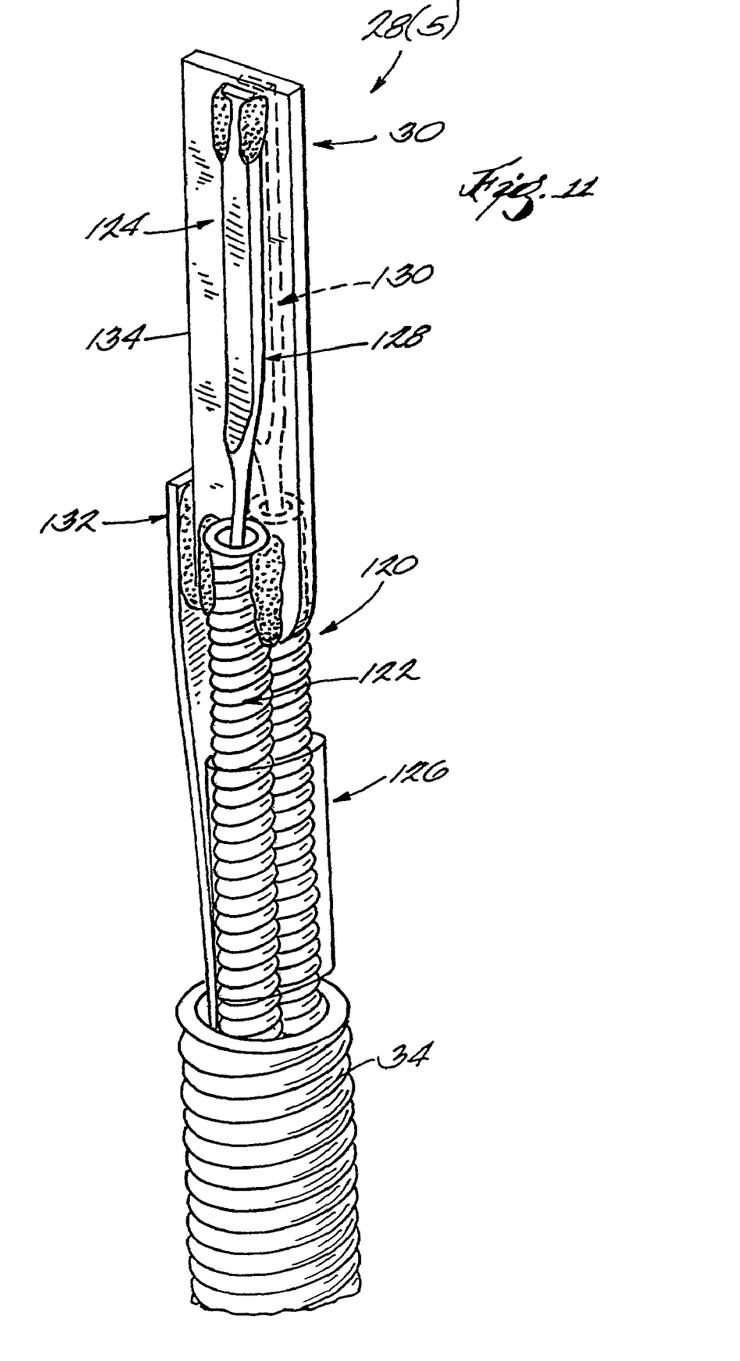
FIG. 11 is a side view of another embodiment of a compound steering assembly that embodies features of the invention.

FIG. 11 shows an alternative embodiment of a compound steering assembly, designated 28(5), that reduces stiffness of the proximal section. The compound steering assembly 28(5) includes two side-to-side guide coils 120 and 122. A distal element 124 is soldered between the distal ends of the guide coils 120 and 122, thereby collectively forming a distal bendable section 30. A PET retaining sleeve 126 preferably holds the guide coils 120 and 122 together orthogonal to plane of the distal element 124.

Distal steering wires 128 and 130 are attached to opposite sides of the distal element 124. The steering wires 128 and 130 pass through the guide coils 120 and 122 and into the main guide coil 34 within the catheter body 14 for attachment to a control element on the handle. By applying tension to a steering wire 128 and 130, the distal element 124 and guide coils 120 and 22 bend as a unified structure in the direction of the tensioned steering wire.

A proximal steering wire 132 is soldered to a transverse edge 134 of the distal element 124. The proximal steering wire 132 also extends into the main guide coil 34 within the catheter body 14 for attachment to another control element on the handle. By applying tension to the proximal steering wire 132, the distal element 124 and guide coils 120 and 122 bend as a unified structure in a direction orthogonal to the direction controlled by the distal steering wires 128 and 130. A second proximal steering wire (not shown) could be soldered to the opposite transverse edge of the distal element 124 for bi-directional steering.

Figures 12, 13:
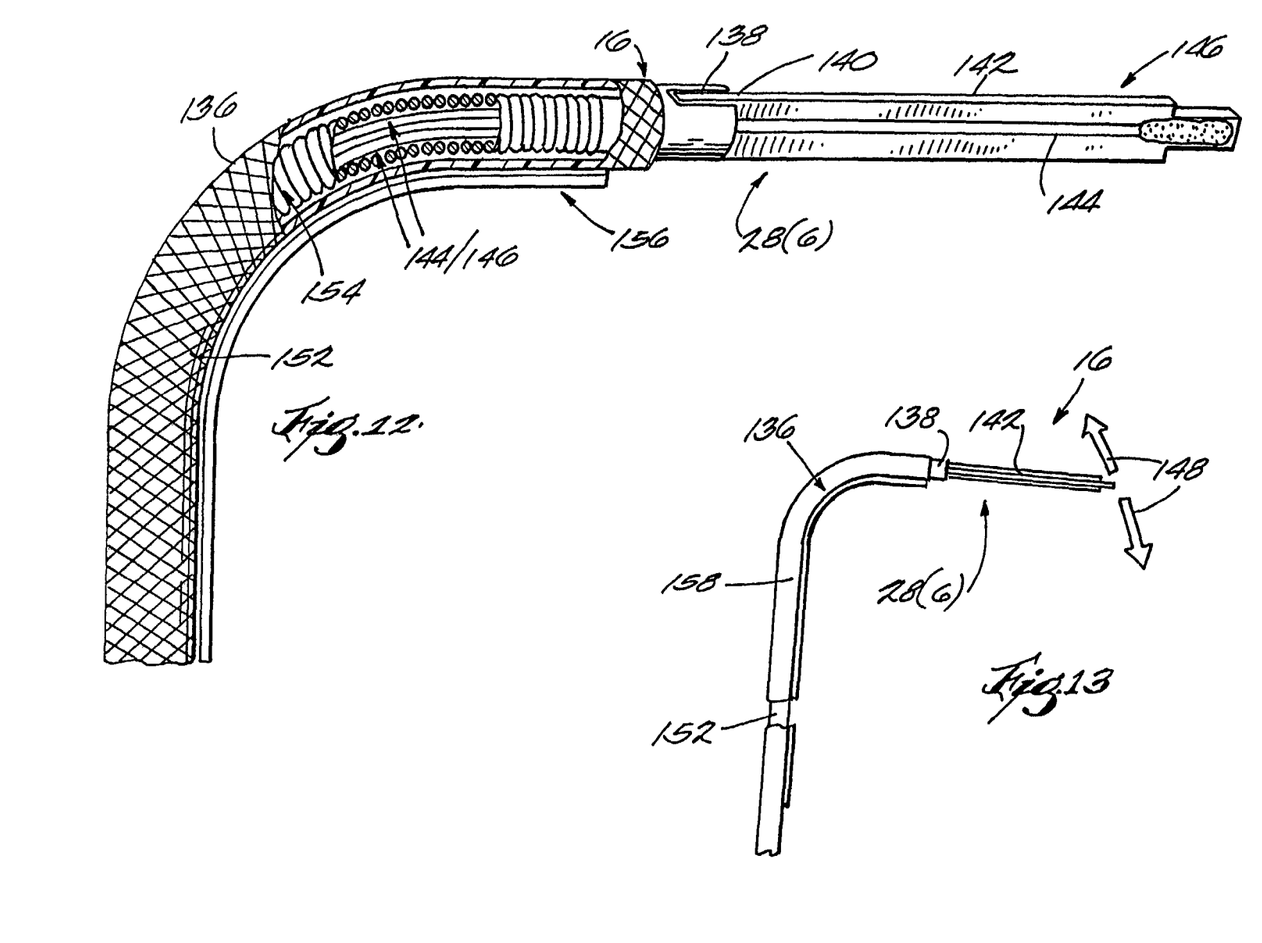
FIGS. 12 and 13 are side views of another embodiment of a compound steering assembly that embodies features of the invention.

FIGS. 12 and 13 show another embodiment of a compound steering assembly, designated 28(6) that embodies features of the invention. The steering assembly 28(6) includes a preformed proximal section 136, which maintains a predefined curve, thereby forming a bend in the distal region 16. The distal end of the preformed proximal section 136 carries a ferrule 138. The ferrule 138 includes a notch 140. A bendable distal spring 142 fits within the notch 140.

The distal spring 142 includes two oppositely attached steering wires 144 and 146. Bi-directional bending of the spring 142 is thereby provided. Alternatively, a single steering wire could be provided for single directional bending.

A sleeve (not shown) made of Kevlar polyester or Kevlar Teflon or plain polyester preferable encircles the junction of the distal spring 142 and the ferrule 138 to strengthen the junction. Further details concerning the sleeve and the attachment of the spring to the distal end of the proximal section are contained in U.S. Pat. No. 5,257,451, which is incorporated herein by reference.

As shown in FIGS. 12 and 13, the notched ferrule 138 holds the distal spring 142 in a plane that is generally orthogonal to the plane of the preshaped bend of the preformed proximal section 136. The distal spring 142 therefore bends in two cross-plane directions, to the right and to the left of the proximal section 136 (as arrows 148 in FIG. 13 show). Still, it should be appreciated that the notched ferrule 138 can be rotated to hold the distal spring 142 in any desired angular relationship with the preshaped proximal section 136.

Figures 14, 15:
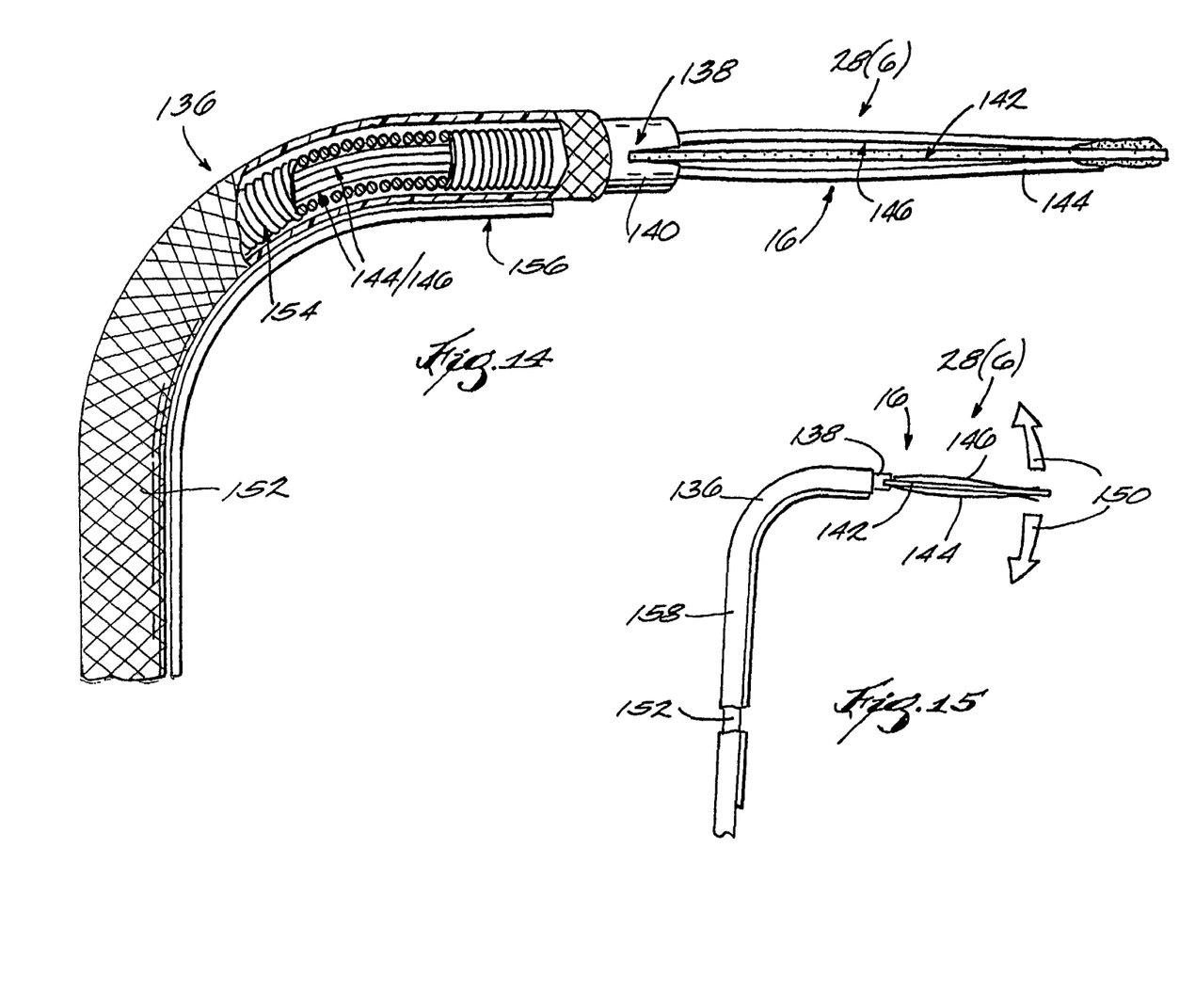
FIGS. 14 and 15 are side views of another embodiment of a compound steering assembly that embodies features of the invention.

For example, FIGS. 14 and 15 show the notch 140 of the ferrule 138 has been rotated to orient the distal spring 142 in generally the same plane as the preformed proximal section 136. In this arrangement, the distal spring 142 is supported for bi-directional, in-plane bending, upward and downward of the preformed proximal section (as arrows 150 in FIG. 15 show).

Figure 16:
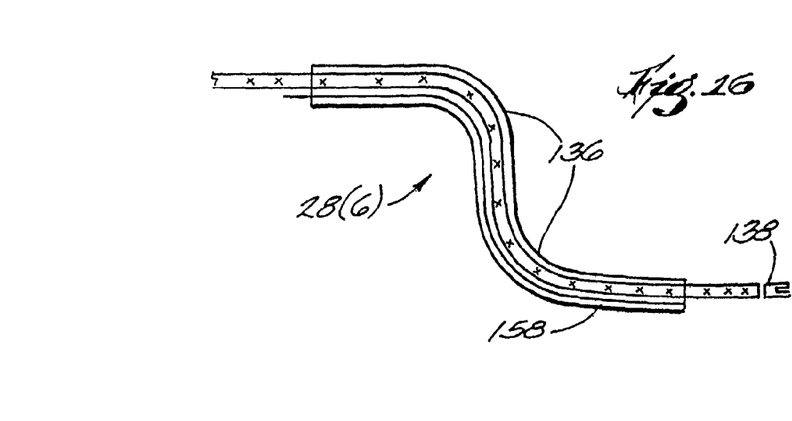
FIG. 16 is a side view of a complex curve that a compound steering assembly made in accordance with the invention can assume.

The proximal section 136 may be preformed into any desired curve, simple (as FIGS. 12 and 13 and FIGS. 14 and 15 show) or complex (as FIG. 16 shows, without a distal spring 142 attached).

In the illustrated simple and complex curve embodiments, the proximal section 136 preferably comprises a braid tube 152 made of polyamide with wire braid, which is thermally formed into the desired shape. The preshaped proximal tube 152 preferably contains within it a guide coil 154, through which the steering wires 144/146 for the distal spring 142 pass. The steering wires 144/146 may also be preshaped like the proximal section to prevent straightening the preformed proximal section.

In the illustrated and preferred embodiments shown in FIGS. 12 and 13 and FIGS. 14 and 15, a flatwire 156 lends additional support to the preformed proximal section 136. The flatwire 156 is formed in a preshaped curve matching corresponding to the proximal section 136. The flatwire 156 is preferably bonded to the exterior of the proximal tube 152. Also preferably, an exterior polyester shrink tube 158 encloses the flatwire 156 and proximal tube 152 to hold them intimately together. The polyester shrink tube 158 can also serve this purpose without first bonding the flatwire 156 to the proximal tube 152. The assembly of the flatwire 156 and shrink tube 158 as just described can also be used in association with the complex curve shown in FIG. 16.

Figure 17:
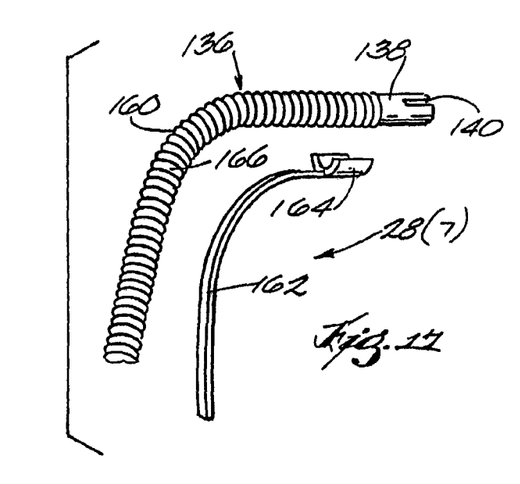
FIGS. 17 and 18 are side views of another embodiment of a compound steering assembly that embodies features of the invention.
Figure 18:
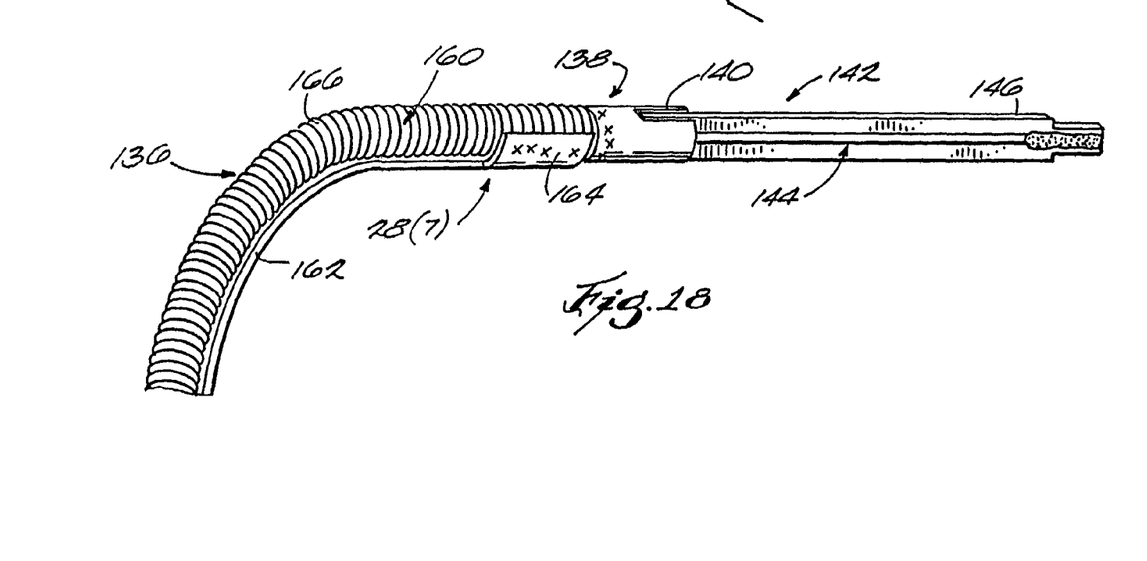

In an alternative embodiment (see FIGS. 17 and 18), a compound steering assembly, designated 28(7) includes a proximal section 160 comprising a guide coil 166 that does not have a preset curvature. In this embodiment, the steering assembly 28(7) includes a flatwire 162 preshaped into the desired curve. The precurved flatwire 162 includes a bracket 164 at its distal end designed to receive and support the guide coil 166. The bracket 164 is spot welded to the guide coil 166, thereby holding the guide coil 166 in a bent condition corresponding to the curve of the flatwire 162. A heat shrink polyester tube (not shown) preferably encircles the flatwire 162 and guide coil 166 to hold them together. The preformed proximal section 136 is thereby formed.

The compound steering assembly 28(7) includes a notched ferrule 138 like that shown in the preceding FIGS. 12 to 16. The ferrule 138 is spot welded to the distal end of the guide coil 166 (see FIG. 18) to receive and support a distal bendable spring 142 and steering wires 144 and 146, in the manner previously shown in FIGS. 12 to 16. As before described, the notch 140 of the ferrule 138 can be rotated to orient the distal spring 142 in any desired orientation, either orthogonal to the curve axis of the preformed proximal section (as FIG. 18 and preceding FIGS. 12 and 13 show), or in plane with the curve axis of the preformed proximal section (as preceding FIGS. 14 and 15 show), or any desired angular relationship in between.

Instead of using a preformed braid tube 152 and/or a flatwire 156/162 to preform the proximal section 136 in the manner above described, the proximal section 136 may take the form of a malleable tube, which can be bent by the physician into the desired simple or complex curvature.

As FIG. 16 represents, the preformed proximal section 136 may be shaped in any simple 2-dimensional or complex 3-dimensional shape. Virtually any curvature can be selected for the proximal section end, provided that the curvature permits unimpeded movement of the steering wires 144/146 for the bendable distal spring 142. Furthermore, the stiffness of the preformed proximal section 136 is controlled so that it readily yields for straightening during introduction, either through the vasculature or a guide sheath.

In vivo experiments demonstrate that the walls of the vasculature themselves provide enough force to straighten the proximal section 136 made according to the invention, to thereby enable easy advancement of the distal region 16 of the catheter body 14 through the vasculature. Guide sheaths may also be used, if desired.

Entry of the distal region 16 of the catheter body 14 into the desired body cavity frees the proximal section 136, and it assumes its predefined shape as previously described. The physician may now further manipulate the distal region 16 by rotating the catheter body 14 and/or bending the distal spring 142 to locate the ablation and/or sensing element(s) 18 at the desired tissue location(s).

The various compound steering assemblies 28(1) to 28(7) that the invention provides make it possible to locate the ablation and/or mapping electrode(s) at any location within the body cavity. With prior conventional catheter designs, various awkward manipulation techniques were required to position the distal region, such as prolapsing the catheter to form a loop within the atrium, or using anatomical barriers such as the atrial appendage or veins to support one end of the catheter while manipulating the other end, or torquing the catheter body. While these techniques can still be used in association with the compound assemblies 28(1) to 28(7), the compound bendable assemblies 28(1) to 28(7) significantly simplify placing electrode(s) at the desired location and thereafter maintaining intimate contact between the electrode(s) and the tissue surface. The compound assemblies 28(1) to 28(7) make it possible to obtain better tissue contact and to access previously unobtainable sites, especially when positioning multiple electrode arrays.

Compound bendable assemblies 28(1) to 28(7) which provide a proximal curved section orthogonal to the distal steering plane allow the physician to access sites which are otherwise difficult and often impossible to effectively access with conventional catheter configurations, even when using an anatomic barrier as a support structure. For example, to place electrodes between the tricuspid annulus and the cristae terminalis perpendicular to the inferior vena cava and superior vena cava line, the distal tip of a conventional the catheter must be lodged in the right ventricle while the catheter is torqued and looped to contact the anterior wall of the right atrium. Compound bendable assemblies 28(1) to 28(7) which can provide a proximal curved section orthogonal to the distal steering plane greatly simplify positioning of electrodes in this orientation. Compound bendable assemblies 28(1) to 28(7) which provide a proximal curved section orthogonal to the distal steering plane also maintain intimate contact with tissue in this position, so that therapeutic lesions contiguous in the subepicardial plane and extending the desired length, superiorly and/or inferiorly oriented, can be accomplished to organize and help cure atrial fibrillation.

A transeptal approach will most likely be used to create left atrial lesions. In a transeptal approach, an introducing sheath is inserted into the right atrium through the use of a dilator. Once the dilator/sheath combination is placed near the fossa ovalis under fluoroscopic guidance, a needle is inserted through the dilator and is advanced through the fossa ovalis. Once the needle has been confirmed to reside in the left atrium by fluoroscopic guidance of radiopaque contrast material injected through the needle lumen, the dilator/sheath combination is advanced over the needle and into the left atrium. At this point, the dilator is removed leaving the sheath in the left atrium.

A left atrial lesion proposed to help cure atrial fibrillation originates on the roof of the left atrium, bisects the pulmonary veins left to right and extends posteriorly to the mitral annulus. Since the lesion described above is perpendicular to the transeptal sheath axis, a catheter which can place the distal steering plane perpendicular to the sheath axis and parallel to the axis of the desired lesion greatly enhances the ability to accurately place the ablation and/or mapping element(s) and ensure intimate tissue contact with the element(s). To create such lesions using conventional catheters require a retrograde procedure. The catheter is advanced through the femoral artery and aorta, past the aortic valve, into the left ventricle, up through the mitral valve, and into the left atrium. This approach orients the catheter up through the mitral valve. The catheter must then be torqued to orient the steering plane parallel to the stated lesion and its distal region must be looped over the roof of the left atrium to position the ablation and/or mapping element(s) bisecting the left and right pulmonary veins and extending to the mitral annulus. This awkward technique often fails to create adequate tissue contact necessary for therapeutic lesions.

Preformed guiding sheaths have also been employed to change catheter steering planes. However, preformed guiding sheaths have been observed to straighten in use, making the resulting angle different than the desired angle, depending on the stiffness of the catheter. Furthermore, a guiding sheath requires a larger puncture site for a separate introducing sheath, if the guiding sheath is going to be continuously inserted and removed. Additional transeptal punctures increase the likelihood for complications, such as pericardial effusion and tamponade.

While various preferred embodiments of the invention have been shown for purposes of illustration it will be understood that those skilled in the art may make modifications thereof without departing from the true scope of the invention as set forth in the appended claims.

Figures 19A, 19B:
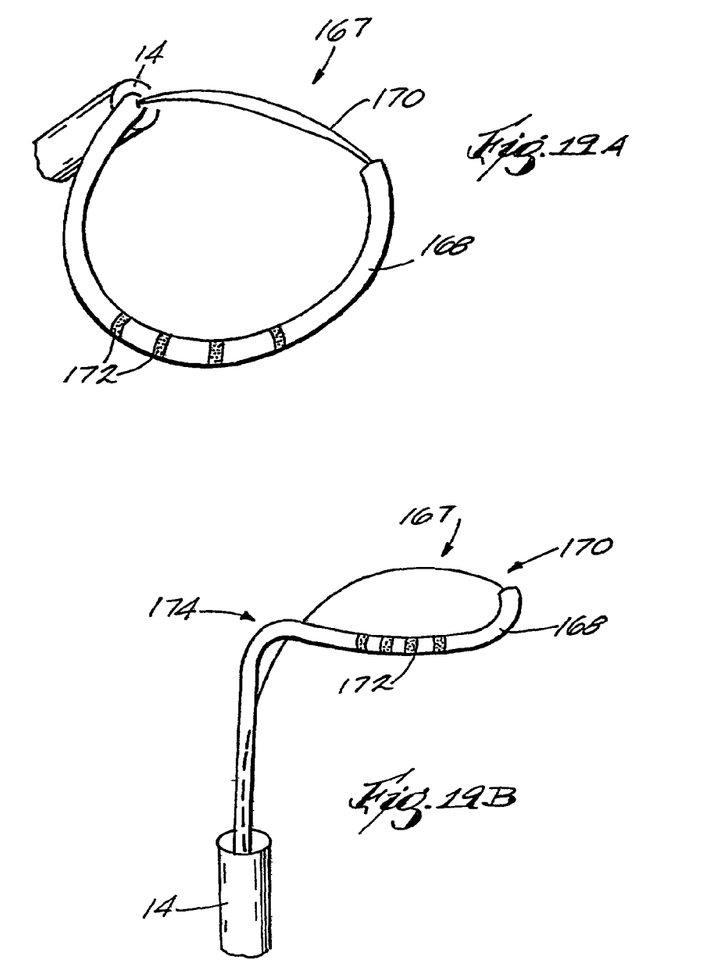
FIGS. 19A to 19C are side views of another embodiment of a compound steering assembly that embodies features of the invention.
Figure 19C:
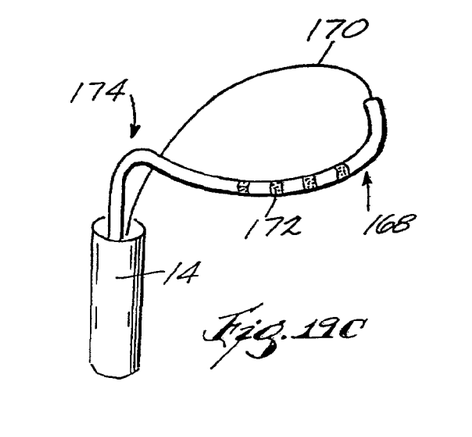

For example, as FIGS. 19A to 19C show a compound loop assembly 168 carried at the distal end of a catheter body 14. The loop assembly 168 comprises at least two loop splines 168 and 170.

The loop spline 168 carries an array of ablation elements 172. According to the features of the invention described above, the loop spline 168 includes a proximal section 174 that is preformed into a desired curvature to access additional planes.

Since the loop spline 168 may be formed from memory elastic materials, the spline 168 may be preformed into any desired shape through mechanically forming the spline 168 and thermally forming the spline 168 in that shape. Preshaped braid tubing or other support may also be included to help maintain the shape of the proximal spline bend 174, as previously described.

As FIGS. 19B and 19C show, the other spline 170 of the loop structure 168 may be retracted or advanced to decrease or increase the loop diameter to affect desired tissue contact and ablation element location.

The two splines 168 and 170 may be fabricated from a single wire made of nickel titanium or other memory elastic material. Alternatively, the two splines 168 and 170 may be fabricated from two or more wires which are connected by a distal tip at a common point. One spline may be attached to the catheter body, or two splines may be attached to the catheter body with another stylet to manipulate the preshaped loop, or both splines may be maneuvered.

Various features of the invention are set forth in the following claims.

What is claimed is:

1. A device, comprising:
   a main body portion defining a proximal end and a distal end and including a preshaped portion having a predefined bend between the proximal and distal ends having a predefined bend and configured to bend out of the predefined bend in response to an application of a force and return to the predefined bend in response to removal of the force;
   a deflectable portion associated with the distal end of the main body portion and deflectable relative to the main body portion; and
   at least one operative element carried by the deflectable portion.

2. A device as claimed in claim 1, wherein the main body portion comprises a catheter body.

3. A device as claimed in claim 1, wherein the preshaped portion comprises a preshaped wire biased to a predetermined curvature.

4. A device as claimed in claim 1, wherein the preshaped portion comprises a thermally formed tube biased to a predetermined curvature.

5. A device as claimed in claim 4, wherein the preshaped portion further comprises a preshaped support biased to the predetermined curvature.

6. A device as claimed in claim 1, wherein the deflectable portion comprises a steering spring.

7. A device as claimed in claim 1, wherein the preshaped portion defines a preshaped portion plane and the deflectable portion deflects within the preshaped portion plane.

8. A device as claimed in claim 1, wherein the preshaped portion defines a preshaped portion plane and the deflectable portion deflects out of the preshaped portion plane.

9. A device as claimed in claim 1, wherein the deflectable portion deflects in at least two directions.

10. A device as claimed in claim 1, wherein the deflectable portion deflects in at least four directions.

11. A device as claimed in claim 1, wherein the at least one operative element comprises an electrode.

12. A device as claimed in claim 1, wherein the at least one operative element comprises a plurality of spaced electrodes.

13. A device as claimed in claim 1, further comprising:
    a steering mechanism, operably connected to the deflectable portion, that bends the deflectable portion relative to the main body portion.

14. A device as claimed in claim 13, wherein the steering mechanism comprises at least one steering wire secured within the deflectable portion.

15. A device as claimed in claim 14, wherein the steering mechanism further comprises a handle connected to the proximal end of the main body portion and to the at least one steering wire.

16. A catheter, comprising:
    a main body portion defining a proximal end and a distal end and including a preshaped portion having a predefined bend located proximal of, and substantially adjacent to, the distal end, the preshaped portion having a predefined bend, defining a preshaped portion plane, and configured to bend out of the predefined bend in response to an application of a force and return to the predefined bend in response to removal of the force;
    a deflectable portion, including a steering spring defining first and second sides and configured to bend in the preshaped portion plane, associated with the distal end of the main body portion and deflectable relative to the main body portion;

first and second steering wires connected to first and second sides of the steering spring; and at least one electrode carried by the catheter deflectable portion.

17. A catheter as claimed in claim 16, wherein the preshaped portion comprises a pre-bent wire biased to a predetermined curvature.

18. A catheter as claimed in claim 16, wherein the preshaped portion comprises a thermally formed tube biased to a predetermined curvature.

19. A catheter as claimed in claim 18, wherein the preshaped portion further comprises a preshaped support biased to the predetermined curvature.

20. A catheter as claimed in claim 16, wherein the steering spring comprises a first portion configured to deflect in the preshaped portion plane and a second portion configured to deflect out of the preshaped portion plane.

21. A catheter as claimed in claim 16, wherein the at least one electrode comprises a plurality of spaced electrodes.

22. A catheter as claimed in claim 16, further comprising a handle connected to the proximal end of the main body portion and to the first and second steering wires.

23. A catheter as claimed in claim 16, wherein the steering spring is substantially flat.

24. A device, comprising:

a main body portion defining a proximal end and a distal end and including a preshaped portion having a predefined bend between the proximal and distal ends;

a deflectable portion, associated with the distal end of the main body portion and deflectable relative to the main body portion, including a steering spring defining a distal end and a proximal end, the proximal end of the steering spring being located distal of the preshaped portion; and at least one operative element carried by the deflectable portion and longitudinally aligned with at least a portion of the steering spring.

25. A device as claimed in claim 24, wherein the main body portion comprises a catheter body.

26. A device as claimed in claim 24, wherein the preshaped portion comprises a preshaped wire biased to a predetermined curvature.

27. A device as claimed in claim 24, wherein the preshaped portion comprises a thermally formed tube biased to a predetermined curvature.

28. A device as claimed in claim 27, wherein the preshaped portion further comprises a preshaped support biased to the predetermined curvature.

29. A device as claimed in claim 24, wherein the preshaped portion defines a preshaped portion plane and the deflectable portion deflects within the preshaped portion plane.

30. A device as claimed in claim 24, wherein the preshaped portion defines a preshaped portion plane and the deflectable portion deflects out of the preshaped portion plane.

31. A device as claimed in claim 24, wherein the deflectable portion deflects in at least two directions.

32. A device as claimed in claim 24, wherein the deflectable portion deflects in at least four directions.

33. A device as claimed in claim 24, wherein the at least one operative element comprises an electrode.

34. A device as claimed in claim 24, wherein the at least one operative element comprises a plurality of spaced electrodes.

35. A device as claimed in claim 24, further comprising:

a steering mechanism, operably connected to the steering spring, that bends the steering spring relative to the main body portion.

36. A catheter as claimed in claim 24, wherein the steering spring is substantially flat.

* * * * *